Figure 1:
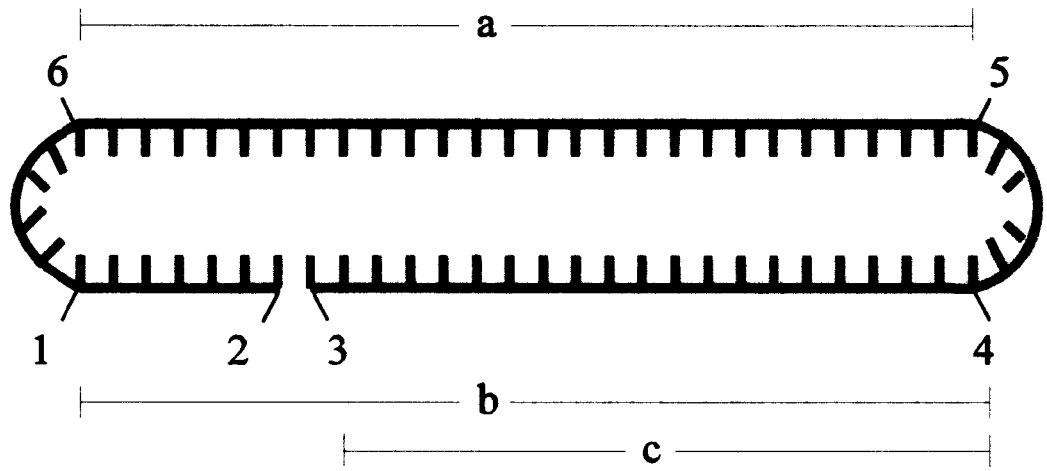

US006010907A

United States Patent [19]
Kmiec et al.

[11] Patent Number: 6,010,907
[45] Date of Patent: Jan. 4, 2000

[54] EUKARYOTIC USE OF NON-CHIMERIC MUTATIONAL VECTORS

[75] Inventors: Eric B. Kmiec, Yardley; Howard B. Gamper, Philadelphia; Allyson D. Cole-Strauss, Narberth, all of Pa.

[73] Assignee: Kimeragen, Inc., Newtown, Pa.

[21] Appl. No.: 09/078,064

[22] Filed: May 12, 1998

[51] Int. Cl.[7] .............................. C12N 5/10; C12N 1/11; C12N 15/11; C12N 15/63

[52] U.S. Cl. ................. 435/455; 435/254.11; 435/320.1; 435/468; 536/23.1

[58] Field of Search .................................... 435/455, 468, 435/320.1, 254.11; 536/23.1

[56] References Cited

U.S. PATENT DOCUMENTS

| | | | |
|---|---|---|---|
| 5,565,350 | 10/1996 | Kmiec ..................................... | 435/463 |
| 5,731,181 | 3/1998 | Kmiec ......................................... | 435/6 |
| 5,760,012 | 6/1998 | Kmiec et al. .............................. | 514/44 |

OTHER PUBLICATIONS

Baumann, P. et al., "Human Rad51 protein promotes ATP–dependent homologous pairing and strand transfer reactions in vitro", 1996, Cell, 87, 757–766.

Baumann. P, & West, SC, "The human Rad51 protein: polarity of strand transfer and stimulation by hRP–A", 1997, EMBO Journal, 16, 5198–5206.

Benson, F. E., et al, "Purification and characterization of the human Rad51 protein, an analogue of *E. coli* RecA", EMBO Journal, 13, 5764–5771, Dec., 1994.

Benson, R. E., et al., "Synergistic actions of Rad51 and Rad 52 in recombination and DNA repair", 1998, Nature, 391, 401–404.

Campbell, C. et al., "Homologous Recombination Involving Small Single–Stranded Oligonucleotides in Human Cells", The New Biologist, vol. 1, pp. 223–227, 1989.

Cole–Strauss, A., et al., "Correction of the Mutation Responsible for Sickle Cell Anemia by an RNA–DNA Oligonucleotide", Science, vol. 273, pp. 1386–1389, Sep. 6, 1996.

Glazer, P. M., et al, "DNA mismatch repair detected in human cell extracts", Jan., 1987, Molecular and Cellular biology, 7(1), 218–224.

Gupta, R. C., et al., "Activities of human recombination protein Rad51", Jan., 1997, Proceedings of the National Academy of the Sciences, 94, 463–468.

Holmes, J., et al., "Strand–specific mismatch correction in nuclear extracts of human and Drosophila melanogaster cell lines", Proceedings of the National Academy of the Sciences, Aug., 1990, 87, 5837–5841.

Hotta, Y., et al., "General recombination mechanisms in extracts of meiotic cells", Chromosoma, 93, 140–151, 1985.

Jessberger, R. & Berg, P., "Repair of Deletions and Double–Strand Gaps by Homologous Recombination in a Mammalian In Vitro System", Molecular and Cellular Biology, 11, 445–457, Jan., 1991.

Kolodner R., "Biochemistry and genetics of eukaryotic mismatch repair", 1996, Genes and Development, 10, 1433–1442.

Kren, B., et al., "Targeted Nucleotide Exchange in the Alkaline phosphatase Gene of HuH–7 Cells Mediated by a Chimeric RNA/DNA Oligonucleotide", Hepatology, vol. 25, pp. 1462–1468, Jun. 1997.

Kren B., et al., "In–vivo site–directed mutagenesis of the factor IX gene by chimeric RNA/DNA oligonucleotides", Nature Medicine, Mar. 1998, 4, 285–290.

Kucherlapati, R., et al., "Homologous Recombination Catalyzed by Human Cell Extracts", Molecular and Cellular Biology, 5(4), 714–720, Apr., 1985.

Lim, S. D. & Hasty, P.A., "A mutation in mouse Rad 51 results in an early embryonic lethal that is suppressed by a mutation in p53", Molecular and Cellular Biology, 16, 7133–7143, Dec. 16, 1996.

Lopez, B. et al., "Homologous recombination intermediates between two duplex DNA catalyzed by human cell extracts", Nucleic Acids Research, 15(14), 1987, 5643–5655 . . . .

Lopez, B.S. et al., "Directional recombination is initiated at a double strand break in human nuclear extracts", Nucleic Acids Research, 20 (3), 501–506, 1992.

Muster–Nassal & Kolodner, "Mismatch correction catalyzed by cell–free extracts of *Saccharomyces cerevisiae*", 1986, Proceedings of the National Academy of the Sciences, 83, 7618–7622.

New, J.H., et al., "Rad 52 protein stimulates DNA strand exchange by Rad51 and replication protein A", Jan., 1998, Nature, 391, 407–410.

Thomas, D. C. et al, "Heterodulex Repair in Extracts of Human HeLa Cells", Feb., 1991, Journal of Biological Chemistry, 266(6), 3744–3751.

Tsuzuki, T., et al, "Targeted disruption of the Rad51 gene leads to lethality in embryonic mice", Proceedings of the National Academy of the Sciences, 93(13), 6236–6240, Jun., 1996.

(List continued on next page.)

*Primary Examiner*—John S. Brusca
*Attorney, Agent, or Firm*—Pennie & Edmonds LLP

[57] ABSTRACT

The invention is based on the reaction of Duplex Mutational Vector in a cell-free system containing a cytoplasmic cell extract and a test plasmid. The reaction specifically converts a mutant kan[r] gene to recover the resistant phenotype in transformed MutS, RecA deficient bacteria. Using this system a type of Duplex Mutational Vector termed a Non-Chimeric Mutational Vector, having no RNA:DNA hybrid-duplex is shown to be an effective substrate for eukaryotic enzymes. The invention concerns the use of Non-Chimeric Mutational Vectors protected from 3' exonuclease attack in eukaryotic cells. Such protection can be conferred by replacement of a tetrathymidine linker by a nuclease resistant oligonucleotide, such as tetra-2'-O-methyl-uridine, to link the two strands of the recombinagenic oligonucleobase.

10 Claims, 1 Drawing Sheet

OTHER PUBLICATIONS

Umar, A., et al., "Defective Mismatch Repair in Extracts of Colorectal and Endometrial Cancer Cell Lines Exhibiting Microsatellite Instability", Journal of Biological Chemistry, 269, 14367–14370.

Varlet, I., et al., "DNA mismatch repair in Xenopus egg extracts: Repair efficiency and DNA repair synthesis for all single base–pair mismatches", Oct., 1990, Proceedings of the National Academy of the Sciences, 87, 7883–7887.

Yamamoto, T., et al. "Strand–specificity in the tranformation of yeast with synthetic oligonucleotides", Genetics, vol. 131, pp. 811–819, 1992.

Yamamoto, T., et al. "Parameters affecting the frequencies of transformation and cotransformation with synthetic oligonucleotides in yeast", Yeast, vol. 8, No. 11, pp. 935–948, Nov. 1992.

Yoon, K., et al., "Targeted gene correction of episomal DNA in mammalian cells mediated by a chimeric RNA–DNA oligonucleotide", Proceedings of the National Academy of the Sciences USA, vol. 93, pp. 2071–2076, Mar., 1996.

Double Hairpin

Single Hairpin With Overhang

EUKARYOTIC USE OF NON-CHIMERIC MUTATIONAL VECTORS

1. FIELD OF THE INVENTION

Chimeraplasty concerns the introduction of directed alterations in a specific site of the DNA of a target cell by introducing duplex oligonucleotides, which are processed by the cell's homologous recombination and error repair systems so that the sequence of the target DNA is converted to that of the oligonucleotide where they are different. The present invention concerns a chimeraplasty method that is practiced in a cell-free system.

2. BACKGROUND TO THE INVENTION

2.1 Chimeraplasty

Chimeraplasty in eukaryotic cells and duplex recombinagenic oligonucleotides for use therein are disclosed in U.S. Pat. No. 5,565,350, issued Oct. 15, 1996, and U.S. Pat. No. 5,731,181, issued Mar. 24, 1998 by E. B. Kmiec (collectively "Kmiec"). The recombinagenic oligonucleotides disclosed by Kmiec contained ribo-type, e.g., 2'-O-methyl-ribonucleotides, and deoxyribo-type nucleotides that were hybridized to each other and were termed Chimeric Mutational Vectors (CMV). A CMV designed to repair a mutation in the gene encoding liver/bone/kidney type alkaline phosphatase was reported in Yoon, K., et al., 1996, Proc. Natl. Acad. Sci. 93, 2071. The alkaline phosphatase gene was transiently introduced into CHO cells by a plasmid. Six hours later the CMV was introduced. The plasmid was recovered at 24 hours after introduction of the CMV and analyzed. The results showed that approximately 30% to 38% of the alkaline phosphatase genes were repaired by the CMV.

A CMV designed to correct the mutation in the human β-globin gene that causes Sickle Cell Disease and its successful use was described in Cole-Strauss, A., et al., 1996, Science 273, 1386. A CMV designed to create a mutation in a rat blood coagulation factor IX gene in the hepatocyte of a rat is disclosed in Kren et al., 1998, Nature Medicine 4, 285–290. An example of a CMV having one base of a first strand that is paired with a non-complementary base of a second strand is shown in Kren et al., June 1997, Hepatology 25, 1462.

U.S. Pat. No. 5,760,012, by E. B. Kmiec, A. Cole-Strauss and K. Yoon, published as WO97/41141, Nov. 6, 1997, and U.S. Pat. No. 5,888,983, disclose methods and CMV that are useful in the treatment of genetic diseases of hematopoietic cells, e.g., Sickle Cell Disease, Thalassemia and Gaucher Disease.

An example of the use of a CMV having one base of a first strand that is paired with a non-complementary base of a second strand is shown in Kren et al., June 1997, Hepatology 25, 1462. In Kren, the strand having the different desired, sequence was the strand having 2'-O-methyl ribonucleotides, which was paired with the strand having the 3' end and 5' end. U.S. Pat. No. 5,565,350 described a CMV having a single segment of 2'-O-methylated RNA, which was located on the chain having the 5' end nucleotide.

Applicants are aware of the following provisional applications that contain teaching with regard to chimeric mutational vectors: By Steer et al., Ser. No. 60/045,288 filed Apr. 30, 1997; Ser. No. 60/054,837 filed Aug. 5, 1997; Ser. No. 60/064,996, filed Nov. 10, 1997; and by Steer & Roy-Chowdhury et al., Serial No. 60/074,497, filed Feb. 12, 1998, entitled "Methods of Prophylaxis and Treatment by Alteration of APO B and APO E Genes."

2.2 Cell-Free Recombination

Various reports of homologous recombination using a cell-free extract have been published.

Hotta, Y., et al., 1985, Chromosoma 93, 140–151 report the use of an extract of yeast, mouse spermatocytes and Lilium to effect homologous recombination between two mutant pBR322 plasmids. One of the plasmids was supercoiled, the second plasmid could be linearized or supercoiled. The maximum rate of recombination was less than 1%. A similar experiment using mutant defective pSV2neo and extracts of EJ cells was reported in Kucherlapati, R. S. et al., 1985, Molecular and Cellular Biology 5, 714–720. The maximum rate of recombination was about 0.2%. Kucherlapati reported an absolute requirement that one of the mutant plasmids be linearized. In contrast Hotta, reported recombination between two circular plasmids, although the rate of recombination between circular and linear plasmids was higher.

The report of Jessberger, R., & Berg, P., 1991, Mol. & Cell. Biol. 11, 445 concerns recombination catalyzed by nuclear extracts between plasmids. It stands in contrast to both of the above in two respects. The rate of recombination reported was about 20%, in contrast to rates of less than 0.5%. In addition Jessberger observed the same rate of recombination between circularized plasmids as between a circularized and a linear plasmid.

A related experiment using human nuclear extracts was reported by Lopez, B. S., et al., 1992, Nucleic Acids Research 20, 501–506. Lopez reported recombination in a cell-free system between a linearized plasmid and an unrelated supercoiled plasmid that is not viable in the subsequent selection conditions. The linearized and supercoiled plasmid each contain a lacZ gene; which is a mutant in the linearized plasmid. The linearized plasmid is cut in the lacZ. gene at a variable distance from the mutation. Homologous recombination between the site of the mutation and the cut, accordingly, results in the circularization of the plasmid that then becomes viable and the gain of lacZ function. Lopez reports no detectable homologous recombination when the cut and the mutation were 15 base pairs apart. Homologous recombination at a low level was observed when that distance was 27 base pairs. No further increase in the rate of homologous recombination was observed when the distance was made greater than 165 base pairs. Lopez et al., 1987, Nucleic Acids Research

2.3 Rad51 and Rad52 Activity in Recombination

Homologous recombination is the process whereby the genes of two chromosomes are exchanged. The rate of homologous recombination between two genetic loci is inversely proportional to their genetic linkage, tightly linked genes rarely recombine. In addition to its genetic function homologous recombination allows a somatic cell to repair DNA damaged by double strand breaks.

The first step in homologous recombination is believed to be synapse formation. A synapse is a DNA molecule in which one chain is hybridized to two other chains. Synapse formation requires an enzymatic activity and energy input from ATP hydrolysis. An artifactual assay in a cell-free system for the enzymatic activity believed to be required for synapse formation is "strand transfer." In a typical strand transfer assay a circular single strand DNA is combined with a linear duplex to produce a "nicked" or relaxed circular duplex and a linear single strand. The Rad51 gene from yeast, mice and humans has been cloned and catalyzes strand transfer. Rad51 is believed to participate in synapse formation. Baumann, P., et al., 1996, Cell 87, 757–766; Gupta, R. C., 1997, Proc. Natl. Acad. Sci. 94, 463–468. The strand transfer activity is further enhanced by the presence of Rad52 protein and replication protein A. Baumann, P., & West, S. C., 1997, EMBO J. 16, 5198–5206; New, J. H., et al., 1998, Nature 391, 407–410; Benson, F. E., et al., 198, Nature 391, 401–404. Although RAD51 protein unlike Rec A binds to duplex DNA, Baumann & West op cit.; Benson, F. E., et al., EMBO J., 13, 5764–5771, in the presence of RAD52, its binding is directed towards single stranded DNA.

In yeast, Rad51 or Rad52 defective individuals are radiation sensitive because of an inability to repair double strand breaks. In mice, Rad51knock out results in embryonic leathality. Tsuzuki, T., et al., Proc. Natl. Acad. Sci. 93, 6236–6240; Lin, S. D., & Hasty, P. A., Mol. Cell. Biol., 16, 7133.

2.4 Cell-Free Mismatch Repair

The intrinsic (thermodynamic) fidelity of DNA replication would lead to an unacceptably high rate of mutation without the presence of an "error correcting" mechanism. Mismatch repair is one such mechanism. In mismatch repair, duplex DNA having a base paired to a non-complementary base is processed so that one of the strands is corrected. The process involves the excision of one of the strands and its resynthesis. Reports of mismatch repair in cell-free eukaryotic systems can be found in Muster-Nassal & Kolodner, 1986, Proc. Natl. Acad. Sci. 83, 7618–7622 (yeast); Glazer, P. M., et al., 1987, Mol. Cell. Biol. 7, 218–224 (HeLa cell); Thomas D. C., et al., 1991, J. Biol. Chem., 266, 3744–3751 (HeLa cell); Holmes et al., 1991, Proc. Natl. Acad. Sci., 87, 5837–5841(HeLa cell and Drosophila). The HeLa and Drosophila cell-free systems required that one strand of the mismatched duplex be nicked for full activity. By contrast, reports of repair in Xenopus egg extracts did not require that the mismatched duplex be nicked. Varlet, I., et al., 1990, Proc. Natl. Acad. Sci. 87, 7883–7887. However, in Varlet the mismatch was repaired in a random fashion, i.e., the strands acted as templates with equal frequency.

Many of the genes required for mismatch repair in yeast and humans have been cloned based on homology with the *E. coli* mismatch repair genes. Kolodner, R., 1996, Genes & Development 10, 1433–1442. Cells having defective mismatch repair genes show genetic instability, termed Replication Error (RER), particularly evident in microsatellite DNA, and malignant transformation. Extracts of RER cells do not have mismatch repair activity. Umar, A., et al., J. Biol. Chem. 269, 14367–14370.

3. BRIEF DESCRIPTION OF THE FIGURES

FIG. 1. An example of the conformation of a double hairpin type recombinagenic oligomer. The features are: a, first strand; b, second strand; c, first chain of the second strand; 1,5' most nucleobase; 2,3' end nucleobase; 3,5' end nucleobase; 4,3' most nucleobase; 5, first terminal nucleobase; 6, second terminal nucleobase.

Figure 2:
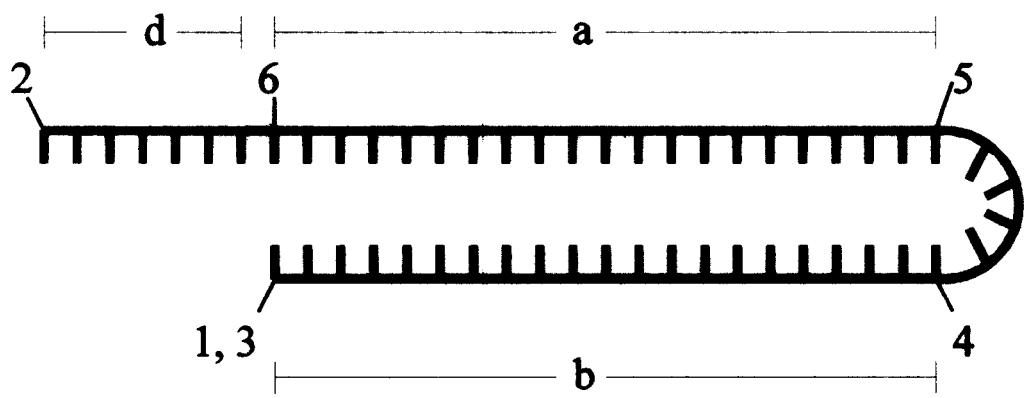

FIG. 2. An example of the conformation of a single hairpin type recombinagenic nucleobase with an overhang. The features are as above with the addition of d, the overhang. Note that the same nucleobase is both the 5' most nucleobase of the second strand and the 5' end nucleobase.

4. SUMMARY OF THE INVENTION

Chimeraplasty is an increasingly important process for the treatment of human disease and the development of useful, genetically engineered plant and animal strains. The development of improved recombinagenic oligonucleotides has been greatly facilitated by the use of bacterial testing systems, which give rapid and quantitative results as described in commonly assigned regular U.S. application Ser. No. 09/078,063, filed May 12, 1998, entitled "Non-Chimeric Mutational Vectors" by R. Kumar et al., and U.S. Provisional Application No. 60/085,191 filed May 12, 1998, entitled "Heteroduplex Mutational Vectors and Use Thereof in Bacteria" by Kumar et al., (hereafter collectively "Kumar") filed on even date herewith, which are hereby incorporated by reference in its entirety. The techniques of Kumar do not address whether the optimal recombinagenic oligonucleotides in bacterial systems are also optimal in eukaryotes. The prior art techniques of in vivo and cell-culture chimeraplasty are not designed for rapid quantitative analysis and are unable to utilize the same recombinagenic oligonucleobases and DNA targets as used in the bacterial systems. Accordingly, an objective of the present invention is an assay that can use DNA targets and recombinagenic oligonucleobases designed for bacterial systems to rapidly evaluate the compatibility between different types of recombinagenic oligonucleotides and the recombination and repair enzymes of different phyla, e.g., do the recombination and mismatch repair enzymes of bacteria, plants, insects and mammals have differing substrate preferences?

A further objective of the invention is an assay that can rapidly determine whether a tissue or cell line is a target for chimeraplasty, i.e, whether it contains the requisite enzymes. A yet further objective is an assay to determine what agents or treatments can alter the level of chimeraplasty activity in a cell line or tissue. A yet further objective of the invention is an assay that can determine whether a compound is an agonist or antagonist of the recombination and repair pathway. An additional objective of the invention is a practical method of making specific genetic changes in a DNA sequence in a cell-free system that is an alternative to polymerase chain reaction PCR-based methods.

The present invention meets these objectives by the unexpected discovery that chimeraplasty can be performed in a cell-free system. The components of the cell-free system are an enzyme mixture containing strand transfer activity and, optionally, a mismatch repair activity, a target DNA sequence and a recombinagenic oligonucleobase. The enzyme mixture can be made by obtaining a cell extract, or a mixture of recombinantly produced purified enzymes. The target DNA sequence is preferably a plasmid that can be used to transform an expression host such as a bacteria. In a preferred embodiment the plasmid is supercoiled. The recombinagenic oligonucleobase is any oligonucleotide or oligonucleotide derivative that can be used to introduce a site specific, predetermined genetic change in a cell. As used herein a DNA duplex consisting of more than 200 deoxyribonucleotides and no nucleotide derivatives is not a recombinagenic oligonucleobase. Typically, a recombinagenic oligonucleobase is characterized by being a duplex nucleotide, including nucleotide derivatives or non-nucleotide interstrand linkers, and having between 20 and 120 nucleobases or equivalently between 10 and 60 Watson-Crick nucleobase pairs. In a preferred embodiment, the recombinagenic oligonucleobase is substantially a duplex and contains a single 3' end and 5' end; accordingly, the strands of the duplex are covalently linked by oligonucleobase or non-oligonucleobase linkers. A further embodiment of the present invention is based on the discovery that the Non-Chimeric Mutational Vectors (NCMV), according to Kumar, are effective substrates for the strand transfer and repair enzymes of eukaryotic and, specifically mammalian cells. Yet further embodiments of the invention are based on the discovery that two types of recombinagenic oligonucleobases, according to Kumar, Heteroduplex Mutational Vectors (HDMV) and vectors having a single segment of ribo-type nucleobases in the strand opposite the strand containing the 3' end nucleobase and 5' end nucleobase, unexpectedly give superior results when used with eukaryotic and specifically in mammalian strand transfer and repair enzymes. The term Duplex Mutational Vectors (DMV) is used herein to refer to CMV, HDMV and NCMV, collectively. Note that a HDMV can be either chimeric or non-chimeric, however, the term CMV does not encompass HDMV.

5. DETAILED DESCRIPTION OF THE INVENTION

According to the present invention a reaction is carried out in a reaction mixture containing an enzyme mixture comprising strand transfer and mismatch repair activities, a DNA target and a recombinagenic oligonucleobase. In one embodiment the DNA target is a mutated antibiotic resistance gene, e.g., tet or neo (kan) of a plasmid and the recombinagenic oligonucleobase is a 2'-O-methyl containing a CMV according to Kmiec, at about a 1:200 molar ratio. The function of the mutant tet or kan is restored by specific alteration of a single base. The reaction is terminated by phenol/chloroform extraction and the extracted plasmid electroporated into RecA or MutS defective bacteria. The extent of modification of the target DNA can be determined from the ratio of the recombinant ($kan^r$ or $tet^r$) colonies to the parental type ($amp^r$). No recombinant colonies, above background, were observed when the plasmid and chimera were reacted separately and recombined after chloroform/phenol extraction. Recombinant colonies were reduced about 90% when extracts of mismatch repair deficient cells (LoVo) were used. These controls indicate that the modification, up to the point of mismatch excision is completed in the reaction mixture. The frequency of recombinant colonies was about 5 per $10^5$ parental colonies using CMV of the type described in Kren et al. Nature Medicine, 1998, 4, 285–290 and Cole-Strauss et al., 1996, Science 273, 1386 (a "Cole-Straus CMV").

As used herein a cell-free enzyme mixture is deemed to have strand transfer and mismatch repair activity when the cell-free mixture can be used to obtain the above described result.

Table I below shows the effects of multiple modifications of the Cole-Strauss CMV in both the bacterial and cell-free eukaryotic systems. There is a very good correlation between the activity of any modification measured in each system. In particular the substitution of 2'-O-methyl uracil for thymidine in the interstrand linkers (variants IV and V), the placement of the mutator only in the 5' strand (variant VIb) and deletion of DNA from the 3' strand significantly improved the performance of the recombinagenic oligonucleobases in both systems.

In both systems the placement of the mutator in the 3' strand (variant VIa) resulted in a substantial loss of function to below one in $10^5$ recombinant colonies. The frequency observed with variant VIa was clearly higher than background. Accordingly, as used herein a recombinagenic oligonucleobase is an oligonucleobase of the type that can provide a rate of recombination in the above cell-free system at least as high as a recombinagenic oligonucleobase made according to variant VIa having the same mutator sequence.

Variant VII with a one base mutator sequence was observed to effect recombination with a frequency of 4.4/$10^5$. This frequency was significantly greater than that observed in the bacterial systems as well as that observed in cultured cells. Without limitation as to theory, this difference is believed to be due to the relative absence of exonucleases and endonucleases from the cell free system.

5.1 The Cell-Free Enzyme Mixture

The cell-free enzyme mixture for the practice of the invention contains the strand transfer and the mismatch repair activities. As used herein the term "cell-free enzyme mixture" indicates that the mixture excludes living cells, and preferably excludes the organelles, e.g., nuclei and mitochondria. The extent of the mismatch repair that is required in the cell-free enzyme mixture depends on the method used to detect the modification of the targeted DNA sequence and the utility.

When the modification is detected by biochemical means, e.g., restriction endonuclease digestion, the mismatch repair activity will include mismatch detection, strand cutting and excision and strand resynthesis to fill the excision and ligation. When the modification is detected in a recombination defective bacteria, e.g., E. coli strain DH10, the strand resynthesis and ligation activities may be omitted from the cell-free enzyme mixture. As used herein "mismatch repair activity" does not include the resynthesis and ligation activities, which may be present in the cell-free enzyme mixture but are not required in most applications.

In certain applications, e.g., to assay the effects of modifications of the recombinagenic oligonucleobase on its efficiency with plant or mammalian enzymes, it is preferred that the mismatch repair activity be provided by the cell-free enzyme mixture. Detection by biochemical means or in a host such as a MutS bacteria, e.g., NR9162, which lack mismatch repair is preferred.

For certain applications, it is desirable to separate the complex of target DNA and recombinagenic oligonucleobase from the uncomplexed target DNA. Separation can be readily accomplished by introducing an affinity ligand, e.g., a biotin, onto the recombinagenic oligonucleobase. In such applications, two cell-free enzyme mixtures can be used, one before and one after the separation. The first mixture should contain only the strand transfer activity and the second need contain only the mismatch repair activity.

The cell-free enzyme mixture can be obtained as a cell extract. A procedure of Li & Kelly can be used. Li., J. J., et alia., 1985, Mol. Cell. Biol. 5, 1238–1246. The Li & Kelly procedure is a "cytoplasmic extract." The cells are mechanically disrupted in hypotonic buffer and the supernatant from centrifugation of 10 min. at 2,000×g and twice of 15 min. at 12,000×g is used. Without limitation as to theory, it is believed that the physiological cellular location of the strand transfer and mismatch repair enzymes is the nucleus but that during preparation there is sufficient loss of these enzymes from the nucleus. Crude nuclear extracts made according to Dignam et al., 1983, Nucleic Acid Research 11, 1475 are not preferred.

A cell-free enzyme mixture that lacks mismatch repair can be obtained from extracts of mutant cells having the replication error phenotype. Umar et al., 1994, J. Biol. Chem. 269, 14367. The cell line LoVo has deleted both alleles of the human MutS homolog (MSH2) and is suitable as a source of strand transfer activity without mismatch repair activity.

In an alternative embodiment the cell-free enzyme mixture can be a composition comprising recombinantly produced enzymes. The recombinant production of a defined enzyme allows for the addition of a known amount of the defined enzyme free of all other enzymes involved in the strand transfer and mismatch repair. When a defined enzyme is added to an extract from a cell that is deficient in that enzyme the result is a defined enzyme mixture with regard to that enzyme. The production of recombinant Rad51 can be accomplished by the methods reported by Gupta, R. C., 1997, Proc. Natl. Acad. Sci. 94, 463–468.

5.2 The Recombinagenic Oligonucleobase

Recombinagenic oligonucleobases for use in a cell-free system can be constructed according to the teaching of U.S. Pat. No. 5,565,350 and U.S. Pat No. 5,731,181. Additionally, recombinagenic oligonucleobases can be made according to the following.

Definitions

The invention is to be understood in accordance with the following definitions.

An oligonucleobase is a polymer of nucleobases, which polymer can hybridize by Watson-Crick base pairing to a DNA having the complementary sequence.

Nucleobases comprise a base, which is a purine, pyrimidine, or a derivative or analog thereof. Nucleobases include peptide nucleobases, the subunits of peptide nucleic acids, and morpholine nucleobases as well as nucleobases that contain a pentosefuranosyl moiety, e.g., an optionally substituted riboside or 2'-deoxyriboside. Nucleotides are pentosefuranosyl containing nucleobases that are linked by phosphodiesters. Other pentosefuranosyl containing nucleobases can be linked by substituted phosphodiesters, e.g., phosphorothioate or triesterified phosphates.

A oligonucleobase compound has a single 5' and 3' end nucleobase, which are the ultimate nucleobases of the polymer. Nucleobases are either deoxyribo-type or ribo-type. Ribo-type nucleobases are pentosefuranosyl containing nucleobases wherein the 2' carbon is a methylene substituted with a hydroxyl, substituted oxygen or a halogen. Deoxyribo-tape nucleobases are nucleobases other than ribo-type nucleobases and include all nucleobases that do not contain a pentosefuranosyl moiety, e.g., peptide nucleic acids.

An oligonucleobase strand generically includes regions or segments of oligonucleobase compounds that are hybridized to substantially all of the nucleobases of a complementary strand of equal length. An oligonucleobase strand has a 3' most (3' terminal) nucleobase and a 5' most (5' terminal) nucleobase. The 3' most nucleobase of a strand hybridizes to the 5' most nucleobase of the complementary strand. Two nucleobases of a strand are adjacent nucleobases if they are directly covalently linked or if they hybridize to nucleobases of the complementary strand that are directly covalently linked. An oligonucleobase strand may consist of linked nucleobases, wherein each nucleobase of the strand is covalently linked to the nucleobases adjacent to it. Alternatively a strand may be divided into two chains when two adjacent nucleobases are unlinked. The 5' (or 3') terminal nucleobase of a strand can be linked at its 5'-O (or 3'-) to a linker which linker is further linked to a 3' (or 5') terminus of a second oligonucleobase strand, which is complementary to the first strand, whereby the two strands form a single oligonucleobase compound. The linker can be an oligonucleotide, an oligonucleobase or other compound. The 5'-O and the 3'-O of a 5' end and 3' end nucleobase of an oligonucleobase compound can be substituted with a blocking group that protects the oligonucleobase strand. However, for example, closed circular oligonucleotides do not contain 3' or 5' end nucleotides. Note that when an oligonucleobase compound contains a divided strand the 3' and 5' end nucleobases are not the terminal nucleobases of a strand.

Conformation

The Duplex Mutational Vectors (DMV) are comprised of polymers of nucleobases, which polymers hybridize, i.e., form Watson-Crick base pairs of purines and pyrimidines, to DNA having the appropriate sequence. Each DMV is divided into a first and a second strand of at least 12 nucleobases and not more than 75 nucleobases. In a preferred embodiment the length of the strands are each between 20 and 50 nucleobases. The strands contain regions that are complementary to each other. In a preferred embodiment the two strands are complementary to each other at every nucleobase except the nucleobases wherein the target sequence and the desired sequence differ. At least two non-overlapping regions of at least 5 nucleobases are preferred.

Nucleobases contain a base, which is either a purine or a pyrimidine or analog or derivative thereof. There are two types of nucleobases. Ribo-type nucleobases are ribonucleosides having a 2'-hydroxyl, substituted 2'-hydroxyl or 2'-halo-substituted ribose. All nucleobases other than ribo-type nucleobases are deoxyribo-type nucleobases. Thus, deoxy-type nucleobases include peptide nucleobases.

In the embodiments wherein the strands are complementary to each other at every nucleobase, the sequence of the first and second strands consists of at least two regions that are homologous to the target gene and one or more regions (the "mutator regions") that differ from the target gene and introduce the genetic change into the target gene. The mutator region is directly adjacent to homologous regions in both the 3' and 5' directions. In certain embodiments of the invention, the two homologous regions are at least three nucleobases, or at least six nucleobases or at least twelve nucleobases in length. The total length of all homologous regions is preferably at least 12 nucleobases and is preferably 16 and more preferably 20 nucleobases to about 60 nucleobases in length. Yet more preferably the total length of the homology and mutator regions together is between 25 and 45 nucleobases and most preferably between 30 and 45 nucleobases or about 35 to 40 nucleobases. Each homologous region can be between 8 and 30 nucleobases and more preferably be between 8 and 15 nucleobases and most preferably be 12 nucleobases long.

One or both strands of the DMV can optionally contain ribo-type nucleobases. In a preferred embodiment a first strand of the DMV consists of ribo-type nucleobases only while the second strand consists of deoxyribo-type nucleobases. In an alternative preferred embodiment the second strand is divided into a first and second chain. The first chain contains no ribo-type nucleobases and the nucleotides of the first strand that are paired with nucleobases of first chain are ribo-type nucleobases. In an alternative embodiment the first strand consists of a single segment of deoxyribo-type nucleobases interposed between two segments of ribo-type nucleobases. In said alternative embodiment the interposed segment contains the mutator region or, in the case of a HDMV, the intervening region is paired with the mutator region of the alternative strand.

Preferably the mutator region consists of 20 or fewer bases, more preferably 6 or fewer bases and most preferably 3 or fewer bases. The mutator region can be of a length different than the length of the sequence that separates the regions of the target gene homology with the homologous regions of the DMV so that an insertion or deletion of the target gene results. When the DMV is used to introduce a deletion in the target gene there is no base identifiable as within the mutator region. Rather, the mutation is effected by the juxtaposition of the two homologous regions that are separated in the target gene. For the purposes of the invention, the length of the mutator region of a DMV that introduces a deletion in the target gene is deemed to be the length of the deletion. In one embodiment the mutator region is a deletion of from 6 to 1 bases or more preferably from 3 to 1 bases. Multiple separated mutations can be introduced by a single DMV, in which case there are multiple mutator regions in the same DMV. Alternatively multiple DMV can be used simultaneously to introduce multiple genetic changes in a single gene or, alternatively to introduce genetic changes in multiple genes of the same cell. Herein the mutator region is also termed the heterologous region. When the different desired sequence is an insertion or deletion, the sequence of both strands have the sequence of the different desired sequence.

The DMV is a single oligonucleobase compound (polymer) of between 24 and 150 nucleobases. Accordingly the DMV contains a single 3' end and a single 5' end. The first and the second strands can be linked covalently by nucleobases or by non-oligonucleobase linkers. In a preferred embodiment the 3' terminal nucleobase of each strand is protected from 3' exonuclease attack. Such protection can be achieved by several techniques now known to these skilled in the art or by any technique to be developed.

In one embodiment protection from 3'-exonuclease attack is achieved by linking the 3' most (terminal) nucleobase of one strand with the 5' most (terminal) nucleobase of the alternative strand by a nuclease resistant covalent linker, such as polyethylene glycol, poly-1,3-propanediol or poly-1,4-butanediol. The length of various linkers suitable for connecting two hybridized nucleic acid strands is understood by those skilled in the art. A polyethylene glycol linker having from six to three ethylene units and terminal phosphoryl moieties is suitable. Durand, M. et al., 1990, Nucleic Acid Research 18, 6353; Ma, M. Y-X., et al.,1993, Nucleic Acids Res. 21, 2585–2589. A preferred alternative linker is bis-phosphorylpropyl-trans-4,4'-stilbenedicarboxamide. Letsinger, R. L., et alia, 1994, J. Am. Chem. Soc. 116, 811–812; Letsinger, R. L. et alia, 1995, J. Am. Chem. Soc. 117, 7323–7328. Such linkers can be inserted into the DMV using conventional solid phase synthesis. Alternatively, the strands of the DMV can be separately synthesized and then hybridized and the interstrand linkage formed using a thiophoryl-containing stilbenedicarboxamide as described in patent publication WO 97/05284, Feb. 13, 1997, to Letsinger R. L. et alia.

In a further alternative embodiment the linker can be a single strand oligonucleobase comprised of nuclease resistant nucleobases, e.g., a 2'-O-methyl, 2'-O-allyl or 2'-F ribonucleotides. The tetraribonucleotide sequences TTTT, UUUU and UUCG and the trinucleotide sequences TTT, UUU, and UCG are particularly preferred nucleotide linkers.

In an alternative embodiment, 3'-exonuclease protection can be achieved by the modification of the 3' terminal nucleobase. If the 3' terminal nucleobase of a strand is a 3' end, then a steric protecting group can be attached by esterification to the 3'-OH, the 2'-OH or to a 2' or 3' phosphate. A suitable protecting group is a 1,2-(ω-amino)-alkyldiol or alternatively a 1,2-hydroxymethyl-(ω-amino)-alkyl. Modifications that can be made include use of an alkene or branched alkane or alkene, and substitution of the ω-amino or replacement of the ω-amino with an ω-hydroxyl. Other suitable protecting groups include a 3' end methylphosphonate, Tidd, D. M., et alia, 1989, Br. J. Cancer, 60, 343–350; and 3'-aminohexyl, Gamper H. G., et al., 1993, Nucleic Acids Res., 21, 145–150. Alternatively, the 3' or 5' end hydroxyls can be derivatized by conjugation with a substituted phosphorus, e.g., a methylphosphonate or phosphorothioate.

In a yet further alternative embodiment the protection of the 3'-terminal nucleobase can be achieved by making the 3'-most nucleobases of the strand nuclease resistant nucleobases. Nuclease resistant nucleobases include peptide nucleic acid nucleobases and 2' substituted ribonucleotides. Suitable substituents include the substituents taught by U.S. Pat. No. 5,731,181, and by U.S. Pat. No. 5,334,711 (Sproat), which are hereby incorporated by reference, and the substituents taught by patent publications EP 629 387 and EP 679 657 (collectively, the Martin Applications), which are hereby incorporated by reference. As used herein a 2' fluoro, chloro or bromo derivative of a ribonucleotide or a ribonucleotide having a substituted 2'-O as described in the Martin Applications or Sproat is termed a "2'-Substituted Ribonucleotide." Particular preferred embodiments of 2'-Substituted Ribonucleotides are 2'-fluoro, 2'-methoxy, 2'-propyloxy, 2'-allyloxy, 2'-hydroxylethyloxy, 2'-methoxyethyloxy, 2'-fluoropropyloxy and 2'-trifluoropropyloxy substituted ribonucleotides. In more preferred embodiments of 2'-Substituted Ribonucleotides are 2'-fluoro, 2'-methoxy, 2'-methoxyethyloxy, and 2'-allyloxy substituted nucleotides.

The term "nuclease resistant ribonucleoside" encompasses including 2'-Substituted Ribonucleotides and also all 2'-hydroxyl ribonucleosides other than ribonucleotides, e.g., ribonucleotides linked by non-phosphate or by substituted phosphodiesters. Nucleobase resistant deoxyribonucleosides are defined analogously. In a preferred embodiment, the DMV preferably includes at least three and more preferably six nuclease resistant ribonucleosides. In one preferred embodiment the CMV contains only nuclease resistant ribonucleosides and deoxyribonucleotides. In an alternative preferred embodiment, every other ribonucleoside is nuclease resistant.

Each DMV has a single 3' end and a single 5' end. In one embodiment the ends are the terminal nucleobases of a strand. In an alternative embodiment, a strand is divided into two chains that are linked covalently through the alternative strand but not directly to each other. In embodiments wherein a strand is divided into two chains, the 3' and 5' ends are Watson-Crick base paired to adjacent nucleobases of the alternative strand. In such strands the 3' and 5' ends are not terminal nucleobases. A 3' end or 5' end that is not the terminal nucleobase of a strand can be optionally substituted with a steric protector from nuclease activity as described above. In yet an alternative embodiment, a terminal nucleobase of a strand is attached to a nucleobase that is not paired to a corresponding nucleobase of the opposite strand and is not a part of an interstrand linker. Such embodiment has a single "hairpin" conformation with a 3' or 5' "overhang." The unpaired nucleobase and other components of the overhang are not regarded as a part of a strand. The overhang may include self-hybridized nucleobases or non-nucleobase moieties, e.g., affinity ligands or labels. In a particular preferred embodiment of DMV having a 3' overhang, the strand containing the 5' nucleobase is composed of deoxy-type nucleobases only, which are paired with ribo-type nucleobase of the opposite strand. In a yet further preferred embodiment of DMV having a 3' overhang, the sequence of the strand containing the 5' end nucleobase is the different, desired sequence and the sequence of the strand having the overhang is the sequence of the target DNA.

A particularly preferred embodiment of the invention is a DMV wherein the two strands are not fully complementary. Rather the sequence of one strand comprises the sequence of the target DNA to be modified and the sequence of the alternative strand comprises the different, desired sequence that the user intends to introduce in place of the target sequence. It follows that the location where the target and desired sequences differ, the bases of one strand are paired with non-complementary bases in the other strand. Such DMV are termed herein Heteroduplex Mutational Vectors (HDMV). In one preferred embodiment, the desired sequence is the sequence of a chain of a divided strand. In a second preferred embodiment, the desired sequence is found on a chain or a strand that contains no ribo-type nucleobases. In a more preferred embodiment, the desired sequence is the sequence of a chain of a divided strand, which chain contains no ribo-type nucleobases.

Internucleobase linkages

The linkage between the nucleobases of the strands of a DMV can be any linkage that is compatible with the hybridization of the DMV to its target sequence. Such sequences include the conventional phosphodiester linkages found in natural nucleic acids. The organic solid phase synthesis of oligonucleotides having such nucleotides is described in U.S. Pat. No. Re: 34,069.

Alternatively, the internucleobase linkages can be substituted phosphodiesters, e.g., phosphorothioates, substituted phosphotriesters. Alternatively, non-phosphate, phosphorus-containing linkages can be used. U.S. Pat. No. 5,476,925 to Letsinger describes phosphoramidate linkages. The 3'-phosphoramidate linkage (3'-NP(O⁻)(O)O-5') is well suited for use in DMV because it stabilizes hybridization compared to a 5'-phosphoramidate. Non-phosphate linkages between nucleobases can also be used. U.S. Pat. No. 5,489,677 describes internucleobase linkages having adjacent N and O and methods of their synthesis. The linkage 3'-ON (CH$_3$)CH$_2$-5' (methylenemethylimmino) is a preferred embodiment. Other linkages suitable for use in DMV are described in U.S. Pat. No. 5,731,181 to Kmiec. Nucleobases that lack a pentosefuranosyl moiety and are linked by peptide bonds can also be used in the invention. Oligonucleobases containing such so-called peptide nucleic acids (PNA) are described in U.S. Pat. No. 5,539,082 to Nielsen. Methods for making PNA/nucleotide chimera are described in WO 95/14706.

5.3 Specific Uses

Heteroduplex Mutational Vectors of the invention and Non-chimeric Mutational Vectors of the invention can be used in any eukaryotic cell in the place of the prior art Chimeric Mutational Vectors. Patent publication WO 97/41141 by Kmiec et al. teaches the use of Chimeric Mutational Vectors, ex vivo as do U.S. Pat. No. 5,565,350 and U.S. Pat. No. 5,731,181. Kren et al., 1998, Nature Medicine 4, 285 provides guidance for the use of Chimeric Mutational Vectors in vivo.

The recombinagenic oligonucleotides can be used in cell-free systems for several purposes, which will be apparent to those skilled in the art. Examples without limitation are as follows.

The effects of modification in the purity, chemistry, size and/or conformation of recombinagenic oligonucleotides can be rapidly and quantitatively tested in cell-free systems. The cell-free system has the further advantages that efficiency of recombination can be measured independently of the efficiency of delivery.

The cell-free system can be used to test compounds that are intended to inhibit or enhance the activity of the enzymes needed for chimeraplasty, in an alternative embodiment test for compounds that replace an enzyme of the mixture. Inhibitory compounds may be competitive or non-competitive inhibitors that act directly on the enzymes involved. Alternatively, the inhibitors can act on the cell from which an extract is made to block the synthesis or accelerate the degradation of an enzyme. These compounds may act by inducing or suppressing the synthesis of the relevant enzymes or may act by inducing post-synthetic modifications that activate or inactivate the relevant enzymes.

The cell-free system can be further used to test the relevance or particular proteins to the mechanism of chimeraplasty. Such testing can, for example without limitation be performed by use of protein-specific monoclonal antibodies to determine whether the protein in question is relevant to chimeraplasty.

A further use of the cell-free system is the specific modification of plasmid, or other isolated DNA molecules. In one embodiment of use for this purpose, the recombinagenic oligonucleobase contains an affinity ligand, such as biotin, that allows the separation of the complex with the target DNA from the uncomplexed target DNA. The chimeraplasty reaction is, in this embodiment, performed using a separate strand transfer step and a mismatch repair step. This embodiment can be used to increase the proportion of modified DNA targets, so that non-selectable modifications can be made without undue expenditure of material and effort in screening. In one embodiment, the receptor for the affinity ligand is bound to a solid phase particle so that the recombinagenic oligonucleobase/target DNA complex is attached to the particle. In the second stage of the reaction the mismatch repair activity results in the modification and release of the target DNA, whereby the supernatant of the second stage of the process is enriched for the modified plasmid.

6. EXAMPLES

Table I below shows the relative numbers of kanamycin and ampicillin resistant colonies using variants of Kany.y to correct a stop-codon causing CG transversion in the kan resistance gene.

The following materials and methods were employed to obtain these data.

Cell-Free Extracts

HuH-7 (Nakabayashi, H., et al., 1982, Cancer Res. 42, 3858) cells are grown in DMEM supplemented with 10% fetal bovine serum to mid log phase, about 5×10⁵ cells/ml. The cells are mechanically dislodged from the tissue culture flask and pelleted at 500×g. The pellet is washed in ice-cold Hypotonic Buffer with sucrose (20 mM HEPES, pH 7.5, 5 mM KCl, 1.5 mM MgCl$_2$, 1 mM DTT, 250 mM sucrose), washed in ice-cold Hypotonic Buffer without sucrose and then resuspended in Hypotonic Buffer at 6.5×10⁷ cells/ml and incubated on ice for 15 min. Thereafter the cells are lysed using a Dounce homogenizer, 3–5 strokes, and thereafter incubated a further 45 min on ice. The lysate is cleared by centrifugation at 10,000×g for 10 min. and the supernatant aliquoted and stored at −80° C. until use.

Reaction Conditions

The cell-free enzyme mixture, plasmid and DMV are reacted in a final volume of 50 μl. The reaction buffer is 20 mM Tris, pH 7.4, 15 mM MgCl$_2$, 0.4 mM DTT, and 1.0 mM ATP. Plasmid, DMV and extract protein final concentrations are 20 μg/ml, 20 μg/ml and 600 μg/ml, respectively. The reaction is run in 500 μl "Eppendorf" tubes. The tubes are prechilled on ice and the reagents added and mixed except for the extract. The extract is then added and the reaction incubated 45 min at 37° C. The reaction is stopped by chloroform/phenol extraction. The nucleic acid is precipitated with 10% (v/v) 3M sodium acetate, pH 4.8 and 2 volumes of absolute EtOH, at −20° C.

Bacterial Transformation

The precipitated, DMV-treated plasmid is dissolved and bacteria are transformed by electroporation according to standard techniques. After electroporation the bacteria are incubated for 1 hr in the absence of antibiotic (kanamycin) and then for 4 hours in the presence of 20% of the selective level of antibiotic.

Analysis

The effectiveness of the DMV can be ascertained from the ratio of the kanamycin resistant colonies and the ampicillin resistant colonies, which is a measure of the recovery of the plasmid and the efficiency of electroporation. The ratio given in the table below is based on data obtained after a 4 hour incubation with a sub-selective level of kanamycin. Such selective incubation results in an increase in $kan^r$ colonies of about 100 fold. The absolute frequencies, which have been corrected for the pre-plating selection are reported.

DMV

The general structure of a Duplex Mutational Vector for the introduction of kanamycin resistance is given below. The intervening segment, 3' homology region, and 5' homology region are designated "I", "H-3'" and "H-5'", respectively. The interstrand linkers are designated "L". An optional chi site (5'-GCTGGTGG-3') and its complement are indicated as X and X' respectively. The 3' and 5' mutator region are single nucleotides indicated as $M^{3'}$ and $M^{5'}$, respectively. Variant I is similar to the Chimeric Mutational Vectors described in Cole-Strauss, 1996, Science 273, 1386, and Kren, 1998, Nature Medicine 4, 285–290. Variant I is referred to as Kany.y elsewhere in this specification. The symbol "--" for a feature of a variant indicates that the feature of the variant is the same as variant I.

The above DMV causes a CG transversion that converts a TAG stop codon into a TAC tyr codon. Note that the first strand of I lacks an exonuclease protected 3' terminus and that the second strand of I is a divided strand, the first chain of which is the desired, different sequence. Variants IV and V are a Chimeric Mutational Vector and a Non-Chimeric Mutational Vector, respectively, having 3' termini exonuclease protected by a nuclease resistant linker (2'OMe-$U_4$). Variants VIa and VIb are Chimeric Heteroduplex Mutational Vectors. Variant VIb is the variant in which the desired, different sequence is found on the first chain, which chain consists of DNA-type nucleotides only.

The table below gives the activities of the variants relative to the variant I in for a bacterial system and gives the frequency of conversion to $kan^r/10^5$ plasmids for a cell-free extract. The background rates were negligible compared to the experimental values except for variant VIa in the cell-free system and bacterial systems and variant VII in bacteria. The data reported for these variants are background corrected. Variants VIa and VII show low or absent activity. Each of variants Ill–V are superior in both systems to variant I, which is of the type described in the scientific publications of Yoon, Cole-Strauss and Kren cited herein above. Variant VIII is the optimal chimera based on inference from these data.

The results shows an excellent correlation between activity in the cell-free extract and activity in the bacterial system. In particular, in both systems variants IV and VIb are superior to Kany.y and in both systems the Non Chimeric Mutational Vectors are active. The only disparity is variant VII, which contains solely deoxynucleotides. Variant VII is active in the cell-free extract but not the bacterial system. Deoxyoligonucleotides have also been found inactive in eukaryotic cells. Without limitation as to theory, applicants believe that the activity of variant VII in the cell-free system is due to the reduced amount of nucleases present in the system compared to cell-containing systems. In particular, applicants have found that a 5'-end labeled 46 nt single strand DNA was not degraded (<1%) by the cell-free extract in a 10 min incubation at 37° C. incubation. A like result was obtained with a 46 bp 5' end labeled linear duplex DNA substrate. The reaction buffer was 2 mM ATP, 1 mM DTT, 25 mM Tris-Acetate, pH 7.15, 5 mM Mg.

TABLE 1

| DMV | $M^{5'}$ | $M^{3'}$ | H5' | I | H3' | L | X (X') | R.A. (bac) | $kan^{r/}$ $10^5$ $amp^r$ cell-free |
|---|---|---|---|---|---|---|---|---|---|
| I | C | G | 2'-OMe | DNA | 2'-OMe | $T_4$ | None | 1 | 6.0 |
| II | — | — | — | — | — | — | chi† | 3.2 | 1.4‡ |
| III | — | — | 2'-OMe | — | — | — | — | 1.6 | 13 |
| IV | — | — | — | — | — | 2'-OMe-$U_4$ | — | 10.0 | 50 |
| V | — | — | DNA | — | DNA | 2'-OMe-$U_4$ | — | 3.0 | 9.8 |
| VIa | G | — | — | — | — | — | — | 0.06* | 0.25 |
| VIb | — | C | — | — | — | — | — | 7.5 | 10.8 |
| VI | — | — | — | — | — | $T_3$ | — | 4.2 | N.D. |
| VII | — | — | DNA | — | DNA | — | — | ~0 | 4.4 |
| VIII | — | C | 2'-OMe | 2'-OMe | 2'-OMe | 2'-OMe-$U_4$ | — | N.D. | N.D. |

*Site Specific Rate
†GCTGGTGG
R.A. (bac) = relative activity (bacteria);
N.D. = Not Determined
‡Result from an independent experiment normalized to other data The sequences of DMV for the introduction of tetracycline resistance is given below:

TetΔ208T

SEQ ID No. 3

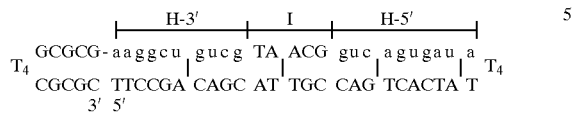

Tet153

SEQ ID No. 4

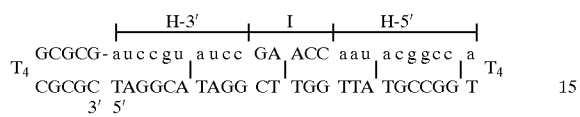

---

We claim:

1. A method of transforming a target DNA sequence into a different, desired sequence in a eukaryotic cell that comprises (A) administering to the cell a duplex mutational vector comprising:
  a. a first oligonucleobase strand of at least 12 linked nucleobases and not more than 75 linked nucleobases, which strand has a first terminal nucleobase and a second terminal nucleobase;
  b. a second oligonucleobase strand having a 3' most nucleobase and a 5' most nucleobase and having a number of nucleobases equal to the first strand, which second strand is optionally divided into a first chain and a second chain; and
  c. a 3' end nucleobase and a 5' end nucleobase; in which
    i. the 3' most and 5' most nucleobases of the second strand are Watson-Crick base paired to the first terminal and the second terminal nucleobase of the first strand, respectively,
    ii. said 3' most nucleobase and said second terminal nucleobase are protected from 3' exonuclease attack, and
    iii. the second strand contains at least two non-overlapping regions of at least 5 contiguous nucleobases that are Watson-Crick base paired to nucleobases of the first strand;

provided that there are not more than two contiguous Watson-Crick base pairs comprised of a ribo-type and a deoxyribo-type nucleobase; and (B) detecting DNA from or in the cell or the progeny thereof having the different, desired sequence.

2. The method of claim 1, wherein each nucleobase of the first strand is Watson-Crick paired to a complementary nucleobase of the second strand.

3. The method of claim 1, wherein the sequence of the first strand comprises the sequence of the different, desired sequence.

4. The method of claim 1, wherein the first terminal nucleobase and the 3' most nucleobase are linked by a linker comprising a moiety selected from the group consisting of 2'-methoxy-uridine, 2'-allyloxy-uridine, 2'-fluoro-uridine, 2'-methoxy-thymidine, 2'-allyloxy-thymidine, 2'-fluoro-thymidine, polyethylene glycol, and trans-4,4'-stilbenecarboxamide.

5. The method of claim 1, wherein the second terminal nucleobase and the 5' most nucleobase are linked by a linker comprising a moiety selected from the group consisting of 2'-methoxy-uridine, 2'-allyloxy-uridine, 2'-fluoro-uridine, 2'-methoxy-thymidine, 2'-allyloxy-thymidine, 2'-fluoro-thymidine, polyethylene glycol, and trans-4,4'-stilbenecarboxamide.

6. The method of claim 1, wherein the second strand is comprised of a first chain and a second chain and the first chain contains no ribo-type nucleobases.

7. The method of claim 6, wherein each nucleobase of the first strand is Watson-Crick paired to a complementary nucleobase of the second strand.

8. The method of claim 6, wherein the sequence of the different, desired sequence is the sequence of the first chain.

9. The method of claim 1, wherein the first chain comprises the 5' end nucleobase.

10. The method of claim 1, wherein the first chain comprises the 3' end nucleobase.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
       (A) LENGTH: 84 base pairs
       (B) TYPE: nucleic acid
       (C) STRANDEDNESS: single
       (D) TOPOLOGY: linear (ii) MOLECULE TYPE: Other (xi) SEQUENCE DESCRIPTION: SEQ ID NO:1:

GCTATTCGGC TASGACTGGG CACAAGCTGG TGGTTTTCCA CCAGCTTGTG CCCAGTCSTA     60

GCCGAATAGC GCGCGTTTTC GCGC                                           84

(2) INFORMATION FOR SEQ ID NO:2:

(i) SEQUENCE CHARACTERISTICS:
       (A) LENGTH: 68 base pairs
       (B) TYPE: nucleic acid
       (C) STRANDEDNESS: single
       (D) TOPOLOGY: linear (ii) MOLECULE TYPE: Other (xi) SEQUENCE DESCRIPTION: SEQ ID NO:2:

GCTATTCGGC TASGACTGGG CACAATTTTT TGTGCCCAGT CSTAGCCGAA TAGCGCGCGT     60

TTTCGCGC                                                             68

(2) INFORMATION FOR SEQ ID NO:3:

(i) SEQUENCE CHARACTERISTICS:
       (A) LENGTH: 68 base pairs
       (B) TYPE: nucleic acid
       (C) STRANDEDNESS: single
       (D) TOPOLOGY: linear (ii) MOLECULE TYPE: Other (xi) SEQUENCE DESCRIPTION: SEQ ID NO:3:

TTCCGACAGC ATTGCCAGTC ACTATTTTTA TAGTGACTGG CAATGCTGTC GGAAGCGCGT     60

TTTCGCGC                                                             68

(2) INFORMATION FOR SEQ ID NO:4:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:4:

```
TAGGCATAGG CTTGGTTATG CCGGTTTTTA CCGGCATAAC CAAGCCTATG CCTAGCGCGT     60

TTTCGCGC                                                             68
```